United States Patent
Han et al.

(10) Patent No.: US 6,573,312 B2
(45) Date of Patent: *Jun. 3, 2003

(54) PHOTO-CURED DENTAL PIT AND FISSURE SEALANT COMPOSITION FOR CARIES PREVENTION

(75) Inventors: Dong-Keun Han, Seoul (KR); Kwang-Duk Ahn, Seoul (KR); Jin-Hee Jeong, Seoul (KR)

(73) Assignee: Dentkist Co. Ltd., Seoul (KR)

( * ) Notice: Subject to any disclaimer, the term of this patent is extended or adjusted under 35 U.S.C. 154(b) by 55 days.

This patent is subject to a terminal disclaimer.

(21) Appl. No.: 09/749,878

(22) Filed: Dec. 29, 2000

(65) Prior Publication Data

US 2002/0072551 A1 Jun. 13, 2002

(30) Foreign Application Priority Data

Oct. 25, 2000 (KR) .......................... 2000-62825

(51) Int. Cl.[7] .............................. A61K 6/083; C08J 3/28
(52) U.S. Cl. ................... 523/116; 523/115; 523/117; 523/438; 522/77; 522/100; 522/109
(58) Field of Search ................ 523/115, 116, 523/113, 117; 522/100, 77, 109

(56) References Cited

U.S. PATENT DOCUMENTS

| | | | |
|---|---|---|---|
| 3,730,947 A | | 5/1973 | Stoffey et al. |
| 4,043,327 A | | 8/1977 | Potter et al. |
| 4,102,856 A | | 7/1978 | Lee, Jr. |
| 4,131,729 A | | 12/1978 | Schmitt et al. |
| 4,572,920 A | * | 2/1986 | Rawls et al. |
| 4,806,381 A | | 2/1989 | Engelbrecht et al. |
| 5,270,350 A | * | 12/1993 | Müller et al. |
| 5,936,006 A | * | 8/1999 | Rheinberger et al. |
| 6,339,113 B1 | * | 6/2002 | Han et al. ................ 522/100 |
| 6,440,573 B1 | * | 8/2002 | Hansen et al. |
| 6,444,725 B1 | * | 9/2002 | Trom et al. |
| 6,455,608 B1 | * | 9/2002 | Jia et al. |

OTHER PUBLICATIONS

"Butylafed Rydroxytoluene", Aldrich Chemical Cat. p. 270, 1988.*

* cited by examiner

Primary Examiner—Tae H. Yoon
(74) Attorney, Agent, or Firm—Oblon, Spivak, McClelland, Maier & Neustadt, P.C.

(57) ABSTRACT

The invention relates to a photo-cured dental pit and fissure sealant composition for caries prevention: i) based on the multifunctional prepolymer mixture of 2,2-bis-(4-(2-hydroxy-3-methacryloyloxypropoxy)phenyl)propane ("Bis-GMA"), which has conventionally been used as dental pit and fissure sealant for caries prevention, and a multifunctional prepolymer formed by substituting hydrogen atoms in hydroxyl group with methacrylate groups in the Bis-GMA molecules; and ii) comprising a diluent, an inorganic filler, a photoinitiation system, and other additives. The dental pit and fissure sealant composition of the present invention is based on a multifunctional prepolymer mixture and has better physical and mechanical properties and biocompatibility than a conventional composition based on Bis-GMA only.

16 Claims, No Drawings

PHOTO-CURED DENTAL PIT AND FISSURE SEALANT COMPOSITION FOR CARIES PREVENTION

BACKGROUND OF THE INVENTION

1. Field of the Invention

1. The present invention relates to a photo-cured dental pit and fissure sealant composition for caries prevention having improved physical and mechanical properties, and biocompatibility, and long time sustainability after operation. More specifically, the invention relates to new photo-cured dental pit and fissure sealant composition for caries prevention, i) based on the multifunctional prepolymer mixture of 2,2-bis-(4-(2-hydroxy-3-methacryloyloxy-propoxy)phenyl)propane ("Bis-GMA") and multifunctional prepolymer formed by substituting hydrogen atoms in hydroxyl group with methacrylate groups in the Bis-GMA molecules; and ii) comprising a diluent, an inorganic filler, a photoinitiation system, and other additives.

2. Description of the Prior Art

2. Eighty-four percent (84%) of all caries occur in the dental pits and fissures of molar chewing surface, i.e., the biting surface, which occupies about 12 % of the total tooth surface. There are dental pits and fissures of various shapes, such as V-, U-, and bottleneck-shaped, in tooth biting surfaces where food residue or intraoral bacteria are deposited, and caries occur. Methods for preventing caries include prophylactic odontomy, invented in 1936, and the prophylactic filling method invented in 1965, both of which have the shortcoming of deleting tooth constitution and are no longer used. Nowadays, dental bacteria control, fluorine use, diet control, the dental pit and fissure sealing method, etc. are being used, of which the dental pit and fissure sealing method is the most recent invention.

3. A dental pit and fissure sealant fills narrow and deep pits and fissures without artificial grinding of the tooth and prevents bacteria or food residues from gathering so as to prevent caries. The dental pit and fissure sealant includes a cyanoacrylate-based sealant, a glass-ionomer cement sealant and a Bis-GMA resin-based sealant.

4. Buonocore announced in the early of 1960s that he invented a cyanoacrylate-based dental pit and fissure sealant that is effective in reducing caries. Accordingly, the cyanoacrylate-based dental pit and fissure sealant were used, but are no longer used since cyanoacrylate quickly polymerizes under moist conditions and is liable to harden so that it is difficult to obtain the satisfactory results.

5. The glass-ionomer cement dental pit and fissure sealant is chemically bonded with calcium ion component of enamel and releases fluorine -ion, which is deposited on enamel so as to prevent caries. However, this sealant bonds more weakly than resin based sealant, which bonds by means of acid corrosion. Also, it is difficult to use the sealant in bottleneck-shaped dental pits and fissures due to high viscosity and a low rate of permeation into said dental pits and fissures; whereas it is effective in V-shaped dental pits and fissures. Also, the glass-ionomer cement has a high initial solubility. Thus, if the glass-ionomer cement is contaminated by contact with moisture before being cured, the cement clinically fails. Also, if too much liquid is used to lower viscosity, the physical properties weaken. Accordingly, the viscosity should not be controlled with liquid.

6. Bis-GMA-based dental pit and fissure sealant invented by Bower is a reaction product of bisphenol A and glycidyl methacrylate. The Bis-GMA-based dental pit and fissure sealant has the advantages of good adhesive strength, low polymerization shrinkage, and intraoral cure easiness. However, because the viscosity of the Bis-GMA-based sealant is too high to permeate into dental pits and fissures, a diluent to lower the viscosity of the sealant, such as methyl methacrylate (MMA) or glycol dimethacrylate (GDMA), should be added to the Bis-GMA-based sealant. The addition of the diluent permits the Bis-GMA-based sealant to be used as the dental pit and fissure sealant. In the present invention, a reaction accelerator activates a reaction initiator and the activated reaction initiator polymerizes Bis-GMA-based dental pit and fissure sealant. In cases where the reaction accelerator is a chemical additive, the sealant is a chemically cured dental pit and fissure sealant. In cases where the reaction accelerator is a visible ray, the sealant is a photo-cured dental pit and fissure sealant. Current dental pit and fissure sealants are mostly Bis-GMA-based sealant.

7. Results from clinical tests on the use of dental pit and fissure sealants to prevent caries shows that the cyanoacrylate-based dental pit and fissure sealant exhibits a 92% reduction in biting surface caries and an 80% rate of preservation 6 months after application. Also, the results shows an 86% reduction in biting surface caries and a 71% rate of preservation 12 months after application. With the glass-ionomer cement dental pit and fissure sealant, however, only 20% of this sealant remains 6 months after application and is completely abraded after 3 years. On the other hand, Bis-GMA resin based dental pit and fissure sealant has the most reliable clinical results and has a caries prevention rate of at least 85% in portions where the sealant is preserved.

8. Bis-GMA resin-based dental pit and fissure sealant itself has high viscosity. Therefore, in order to reduce the viscosity of the sealant, a diluent is added. Bis-GMA resin-based dental pit and fissure sealants are classified as being a chemically-cured or self-cured sealants, or as photo-cured sealants depending on the curing method. Also, depending on the addition of the inorganic filler, sealants are classified as either an inorganic filler-added sealant or an inorganic filler non-added sealant. The chemically cured sealant is mostly the inorganic filler non-added sealant, and the photo-cured sealant is divided into the inorganic filler added sealant and the inorganic filler non-added sealant. The chemically cured sealant has a satisfactory permeation rate, but has the shortcomings of high water absorption, heat expansion, and abrasion. On the other hand, the inorganic filler-added sealant of the photo-cured sealant has a low permeation rate, and good physical properties, such as very low levels of water absorption, heat expansion, and abrasion.

9. A photo-cured dental pit and fissure sealant composition for caries prevention comprises an inorganic filler, such as a surface treated silica, a prepolymer of multifunctional methacrylate, a diluent, a photoinitiation system (a photoinitiator and a reductant), and other additives. The composition should meet the requirements of a viscosity low enough to permeate into a base portion of the dental pit and fissure, which provides a high caries prevention effect, the mechanical strength to support the high biting pressure generated when chewing food, an abrasion rate low enough to extend the preservation time, a coefficient of heat expansion similar to the tooth, and a polymerization shrinkage low enough to inhibit exfoliation from the tooth upon polymerization-curing. Together with its physical properties, the composition should also be the same color and gloss of the natural tooth, and provide a natural tonguetouch feeling. The dimethacrylate, 2,2-bis-(4-(2-hydroxy-3-methacryloyloxypropoxy)phenyl)propane (Bis-GMA) is most generally used as a prepolymer of a photo-cured dental pit and fissure sealant composition for caries prevention. Bis-GMA is principally low in volatility and polymerization shrinkage. A polymer prepared from Bis-GMA has the advantages of superior strength. Thus, Bis-GMA is used as a matrix resin. U.S. Pat. No. 4,102,856, U.S. Pat. No. 4,131,729, and U.S. Pat. No. 3,730,947 and so on describe the use of Bis-GMA. Also, the dental pit and fissure sealant should permeate into the base portion of the dental pit and fissure to improve caries prevention effect, which requires the addition of a diluent, such as triethylene glycol dimethacrylate (TEGDMA). The dental pit and fissure sealant is abraded due to the chewing of food, and the brushing of and rubbing of a person's teeth. In order to provide a sealant with abrasion resistance, an inorganic filler, such as silica, alumina, calcium, and strontium, is added to the sealant (U.S. Pat. No. 4,043,329 and U.S. Pat. No. 4,806,381).

10. As mentioned above, although the Bis-GMA-based dental pit and fissure sealant composition has been used, it still needs to be improved with respect to water absorption, dental pit and fissure permeation, physical properties, and aesthetics.

SUMMARY OF THE INVENTION

11. It is an object of the invention to provide a photo-cured dental pit and fissure sealant composition for caries prevention having higher conversion of photo-cured substance, greater strength, and hardness, improved physical and mechanical properties, such as low polymerization shrinkage and water absorption, and improved biocompatibility in comparison with conventional dental pit and fissure sealant compositions based on Bis-GMA resin.

12. Other objects and advantages of the invention will be clarified in the following detailed description of the invention provided below.

DETAILED DESCRIPTION OF THE INVENTION

13. Hereinafter, the present invention is described in detail.

14. The object of the invention is achieved by means of a photo-cured dental pit and fissure sealant composition for caries prevention that i) has improved physical and mechanical properties and biocompatibility;

ii) is based on the multifunctional prepolymer mixture of 2,2-bis-(4-(2-hydroxy-3-methacryloyloxypropoxy)phenyl)propane ("Bis-GMA") and at least one multifunctional prepolymer containing multimethacrylate groups formed by substituting hydrogen atoms in hydroxyl groups with methacrylate groups in the Bis-GMA molecules; and iii) comprises an adequate amount of a diluent, an inorganic filler, a photoinitiation system and other additives.

15. Bis-GMA has been most frequently used as a prepolymer for dental restoration because of its superior physical properties, such as its high strength after curing. The Bis-GMA molecule has two hydroxyl groups that play a role in promoting an affinity between the organic resin and the inorganic filler, whereas said hydroxyl groups have a property to absorb water due to their high hydrophilicity. In cases where an organic resin absorbs water, the physical properties and aesthetics of a photocured substance is gradually reduced. Thus, if a polymerized resin is swelled by water-absorption, the binding force between it and the filler is weakened such that the filler particle is likely to separate from the resin. The photocured substance is weakened with respect to its physical properties, such as its strength and abrasion resistance. In addition, cytotoxicity is caused, and food is absorbed into the restored substance and becomes discolored. Also, the dental pit and fissure sealant should completely permeate into the minute pores of the acid-corroded enamel and the dental pits and fissures in order to be sufficiently preserved and to provide satisfactory clinical results. If it has a higher perrmeation rate, the sealant can adhere more closely to the surface of the enamel and can permeate into the base portion of the dental pit and fissure so as to prevent caries. The Bis-GMA-based dental pit and fissure sealant has the advantages of good adhesive strength, low polymerization shrinkage, and intraoral cure easiness. However, since the viscosity of Bis-GMA-based sealant is too high to permeate into dental pits and fissures, a diluent to lower the viscosity of the sealant, such as methyl methacrylate (MMA) or glycol dimethacrylate (GDMA), should be added to the Bis-GMA-based sealant. A large quantity of the diluent, however, may cause a weakening of the physical properties of the Bis-GMA-based dental pit and fissure sealant.

16. The present inventors have conducted extensive research to improve the aforesaid problems of conventional photo-cured dental sealant photopolymerizable restoration material prepared solely form Bis-GMA prepolymers. We have found that a photo-cured dental pit and fissure sealant composition for caries prevention can be prepared from a prepolymer mixture of Bis-GMA and trifunctional methacrylate prepolymer (Tri-GMA) and/or tetrafunctional methacrylate prepolymer (Tetra-GMA) having reduced hydrophilicity that is formed by substituting at least one hydrogen atom in the two hydroxyl groups with methacrylate groups in the Bis-GMA molecule. We have also found that the mixed prepolymer mixture has low viscosity so that the amount of diluent to be added may be reduced, which reduces the deterioration of physical and mechanical properties and aesthetics of the resulting dental pit and fissure sealant. We have confirmed that the resulting dental pit and fissure sealant has lower viscosity than the dental pit and fissure sealant based on Bis-GMA in that it permeates into the base portion of the cavity and fissure and has an effect of preventing caries.

17. The first embodiment of the present invention provides a photo-cured dental pit and fissure sealant composition for caries prevention comprising:

18. (A) 15 to 80 wt % of the prepolymer mixture comprising 2,2-bis-(4-(2-hydroxy-3-methacryloyloxypropoxy)phenyl)propane ("Bis-GMA") of formula 1:

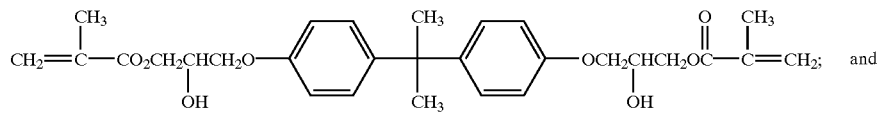

Tri-GMA of formula 2:

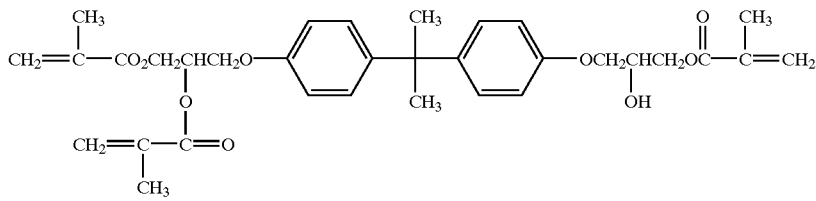

(B) 5 to 50 wt % of a diluent;
(C) 1 to 40 wt % of an inorganic filler;
(D) a photoinitiation system; and
(E) other additives,
wherein the wt % of all the components are based on the total weight of the composition.

19. In accordance with the first embodiment, the weight ratio of Bis-GMA of formula 1 to Tri-GMA of formula 2 is 95:5 to 5:95.

20. The second embodiment of the present invention provides a photo-cured dental pit and fissure sealant composition for caries prevention comprising:
(A) 15 to 80 wt % of the prepolymer mixture comprising Bis-GMA of formula I and Tetra-GMA of formula 3:

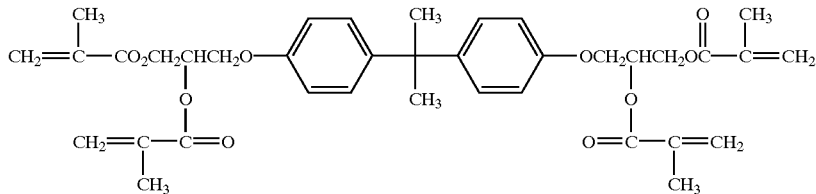

(B) 5 to 50 wt % of a diluent;
(C) 1 to 40 wt % of an inorganic filler;
(D) a photoinitiation system; and
(E) other additives,
wherein the wt % of all the components are based on the total weight of the composition.

21. In accordance with the second embodiment, the weight ratio of Bis-GMA of formula 1 to Tetra-GMA of formula 3 is 95:5 to 5:95.

22. The third embodiment of the present invention provides a photo-cured dental pit and fissure sealant composition for caries prevention comprising:
(A) 15 to 80 wt % of the prepolymer mixture of Bis-GMA of formula 1, Tri-GMA of formula 2, and Tetra-GMA of formula 3;
(B) 5 to 50 wt % of a diluent;
(C) 1 to 40 wt % of an inorganic filler;
(D) a photoinitiation system; and
(E) other additives,
wherein the wt % of all the components are based on the total weight of the composition, and the prepolymer mixture consists of 90 to 5 wt % of Bis-GMA of formula 1, 90 to 5 wt % of Tri-GMA of formula 2, and 90 to 5 wt % of Tetra-GMA of formula 3 on the basis of the total weight of the prepolymer mixture.

23. In accordance with the photo-cured dental pit and fissure sealant composition for caries prevention of the invention, Tri-GMA of formula 2 and Tetra-GMA of formula 3, constituting the prepolymer mixture, may be synthesized by substituting at least one hydrogen atoms in the two hydroxyl groups with methacrylate group in Bis-GMA molecules of formula 1. Thus, scheme 1 shows that Tri-GMA and Tetra-GMA may be quantitatively synthesized by reacting Bis-GMA with methacryloyl chloride in the presence of an organic amine, for example, triethylamine.

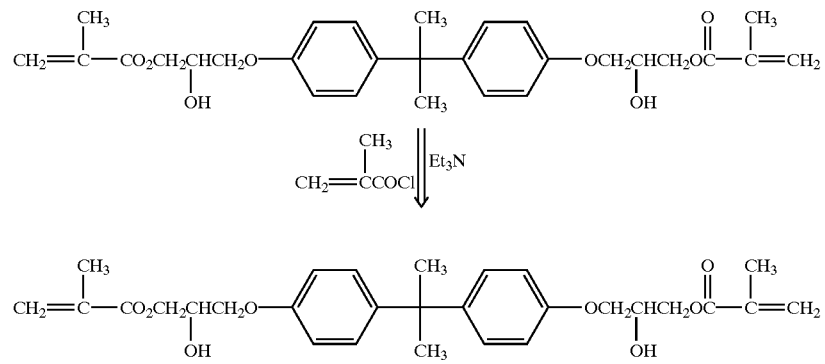

-continued

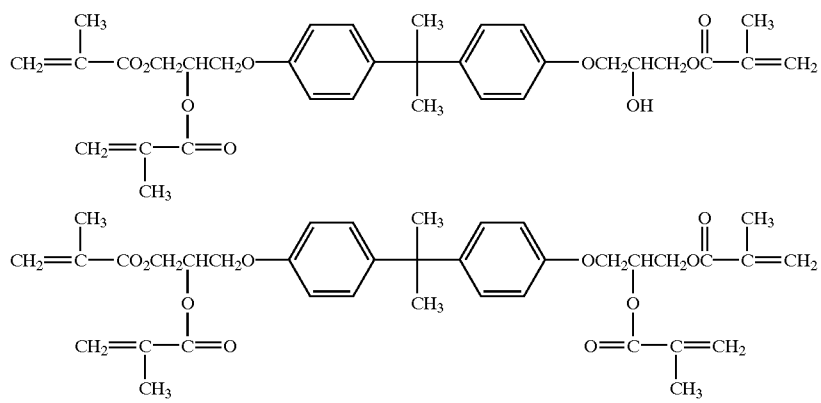

24. The synthesized multifunctional prepolymer mixture is separated into Bis-GMA, Tri-GMA, and Tetra-GMA, through a column using a developer of mixture of ethyl acetate and n-hexane (50:50 weight ratio).

25. In accordance with the present invention, the photo-cured dental pit and fissure sealant composition comprises a prepolymer mixture in an amount of 15 to 80 wt % of the total weight of the composition.

26. In accordance with the present invention, the composition comprises a diluent to reduce the viscosity of the prepolymer mixture. The suitable examples of the diluent are methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexanediol dimethacrylate, 1-methyl-1,3-propanediol dimethacrylate or 1,6-bis(methacryloloxy-2-ethoxycarbonylamino)-2,2,4-trimethylhexane. The composition comprises a diluent in an amount of 5 to 50 wt % of the total weight of the composition.

27. In accordance with the present invention, the composition comprises an inorganic filler in order to improve two-body abrasion resistance and decrease water absorption and heat expansion of the composition. The inorganic filler is preferably silica, quartz, barium glass, barium glass/silica, barium glass mixture, quartz/barium glass, zirconia/silica, silica mixture, alumino silicate, lithium alumino silicate and barium aluminosilcate with a particle size of 0.1 nm to 50 um, surface-treated with a silane coupling agent, and added in an amount of 1 to 40 wt % of the total weight of the composition.

28. In order to surface-treat the inorganic filler, a silane coupling agent is primarily used. The representative examples are γ-methacryloxy propyl trimethoxysilane (γ-MPS), dimethyl dichlorosilane, hexamethylene disilazane, dimethyl polysiloxane and so on.

29. The dental pit and fissure sealant of the present invention is exposed to visible rays that are unharmful to the human body to form a radical from a photoinitiator and a catalyst. Said radical initiates polymerization of a monomer for curing the composition. Polymerization primarily occurs by exposure of a photoinitiator such as, α-diketone aliphatic and aromatic carbonyl compound and tert-amine catalyst to the visible ray under a wavelength ranging from 400 to 500 nm. The photoinitiation system consists of a photoinitiator and a reductant. The photoinitiator is preferably camphorquinone (CQ, and added in an amount of 0.1 to 10 wt % of the total weight of the composition. If CQ is photo-excited to extract hydrogen from the reductant, the reductant practically initiates radical polymerization. A reductant such as N,N-dimethylaminoethyl methacrylate (DMAEMA) or ethyl ρ-dimethyl aminobenzoate (EDMAB) is added in an amount of 0.1 to 10 wt % on the basis of the total weight of the composition.

30. Other additives, such as a polymerization inhibitor, a lightstabilizer, an antioxidant, or a pigment may also be added to conform the color of the dental pit and fissure sealant. A polymerization inhibitor, such as hydroquinone (HQ), hydroquinone monoethyl ether or hydroquinone monoethyl ether, may be added in an amount of 0.1 to 10 wt % of the total weight of the composition. A lightstabilizer, such as 2-(2H-benzotriazol-2-yl)-p-cresol (Tinuvin P) may be added in an amount of 0.01 to 5 wt % of the total weight of the composition. An antioxidant, such as ethylenebis (oxyethylene)bis-(3-(5-tert-butyl-4-hydroxy-m-tolyl)-propionate) (Irganox 245) and 2,6-di-tert-butyl-4-methyl phenol (butylated hydroxytoluene (BHT)), may be added in an amount of 0.01 to 5 wt % of the total weight of the composition. Inorganic pigments of yellow, navy blue, or red colored-iron oxides and titanium dioxide may be added in an amount of 0.001 to 5 wt % on the basis of the total weight of the composition.

31. The physical properties of the specimen from the resulting dental pit and fissure sealant composition are estimated as follows:

1) Photoconversion

32. Photopolymerization efficiency caused by the visible ray is estimated by means of infrared absorption spectroscopy. The conversion of methacrylate monomer is calculated by measuring the decreased area of the absorption band at 1638 cm$^{-1}$ by the aliphatic double bond on the basis of the area of the absorption band at 1609 cm$^{-1}$ by the aromatic ring.

2) Flexural Strength

33. A 25 mm (length)×2.5 mm (width)×2.0 mm (thickness) mold is filled with test material which is flowed into the mold little by little in order to prevent the occurrence of air bubbles. Subsequently, the upper and lower sides of the material are photopolymerized with a photo irradiator and abraded with a sandpaper. The material is then stored at 37° C., relative humidity of 100% for 24 hours. By applying a compression on three points of a specimen at rate of 0.1 mm/sec in tensile tester, the maximum weight up to the fracture of the specimen is measured, and 3-point bending strength (FS) is calculated by the following formula.

$$\text{Flexural Strength (MPa)} = \frac{3 \times \text{maximum weight} \times \text{the length between the supporter}}{2 \times \text{area of specimen} \times \text{height of specimen}} = \frac{3Pl}{2bh^2}$$

3) Water Absorption and Solubility

34. A dental pit and fissure sealant composition is made into about a 6 cm (diameter)×3 mm (height) specimen, which is cured. The weight of the cured specimen is measured, and then the cured specimen is dipped into distilled water at 37° C. After every 24 or 48 hours, the specimen is then taken out, water is removed from the specimen, and the weight of the specimen is measured. Moisture absorption is calculated by the following formula.

$$\text{Water absorption (\%)} = \frac{(\text{weight after dipping} - \text{weight after cure before dipping})}{\text{weight after cure before dipping}} \times 100$$

35. In order to measure solubility, the specimen is taken out, and water is removed from the specimen. The specimen is completely dried again in a desiccator to have uniform weight, and the weight of the specimen is measured. Solubility is calculated by the following formula.

$$\text{Solubility (\%)} = \frac{(\text{weight after cure before dipping} - \text{weight after dipping and complete drying})}{\text{weight after cure before dipping}} \times 100$$

4) Two-body abrasion

36. A 6 mm (diameter)×2 mm (thickness) specimen is prepared and abraded with an abrasion tester to have parallel upper and lower sides. The thickness of the specimen is measured up to 0.1 μm with a micrometer. The specimen is again placed into the abrasion tester in order to be alternatively traveled 10 m on No. 400 sandpaper under the weight of 250 g. The weight of the specimen is again measured. Two-body abrasion is evaluated with thickness decrease value and weight change value before and after the measurement.

5) Surface Hardness

37. A celluloid strip is placed between two glass slides, and sealant is placed between the celluloid strip and a glass slide, which is compressed to form a plate (2 mm (thickness)) having parallel upper and lower surfaces, and then photopolymerized for 20 seconds, with the upper and lower surfaces each being photopolymerized for 10 seconds. Vickers hardness is measured under the weight of 100 g for 10 seconds with a minute durometer.

6) Diametral Tensile Strength

38. The diametral tensile strength measurement method, in which stable compression stress is applied to a specimen instead of direct tensile strength, is used especially in the measurement of the physical properties of dental material. In this method, a disk shaped specimen is laid horizontally, and weight compression is applied to the specimen to cause tensile stress inside the specimen. A 6 mm (diameter)×3.6 mm (thickness) specimen is prepared, and stress is applied to the specimen in a cross-head speed of 0.1 mm/sec with a tensile tester until the specimen is fractured. The diametral tensile strength is calculated by the following formula.

$$\text{Diametral tensile strength (DTS)} = \frac{2 \times \text{maximum load}}{\pi \times \text{diameter of specimen} \times \text{thickness of specimen}}$$

7) Cytotoxicity

39. The cytotoxicity of a dental pit and fissure sealant is estimated by comparing the toxicity degree according to the agar layered plate method. 10 mm (diameter)×2 mm (thickness) specimen is tested using polyvinylchloride [PVC, response rate: 4/4] as the positive control group and polyethylene (PE) as the negative control group. The cell lysis ratio is measured in a discolored region of the specimen using an L-929 cell suspension and an Eagle's agar medium and is indicated in a zone index and lysis index, from which a response index (RI=zone index/lysis index) is calculated. Cytotoxicity is evaluated from RI value. The lower value means a lower toxicity.

TABLE 1

| Definition of each index value | |
|---|---|
| Index | Definition |
| 0 | Discolored area |
| 1 | None permeate under the specimen |
| 2 | The limited area under the specimen |
| 3 | Area diffused from sample <0.5 cm |
| 4 | Are diffused from sample <1 cm |
| 5 | Area diffused from sample ≧1 cm, <total area |
| Lysis Index | Lysis area |
| 0 | None |
| 1 | <20% |
| 2 | 20–40% |
| 3 | 40–60% |
| 4 | 60–80% |
| 5 | ≧80% |

TABLE 2

| Evaluation of cytotoxicity | | |
|---|---|---|
| Scale | RI | Cytotoxicity |
| 0 | 0/0 | None |
| 1 | 1/1 | Weak |
| 2 | 2/2 to 3/3 | Medium |
| 3 | 4/4 to 5/5 | Severity |

40. The present invention is illustrated in detail by the examples given below. However, the examples presented here are for illustrative purposes only and should not be construed as limiting the invention.

Example 1

Preparation of multifunctional prepolymer

41. Bis-GMA (51.2 g, 0.1 mol) was dissolved in methylene chloride (50 ml) and 10.2 g of triethylamine (0.1 mol) was subsequently added. Methacryloyl chloride (7.9 g, 0.75 mol) was slowly added while the solution was stirred in an ice bath. The solution was then stirred at room temperature and precipitated salt was filtered out and removed. A filtrate was washed with distilled water, dehydrated, and distilled under reduced pressure to quantitatively obtain a viscous liquid. The result of the component ratio of the obtained multifunctional prepolymer mixture showed that Bis-GMA of formula 1, Tri-GMA of formula 2, and Tetra-GMA of formula 3 were obtained with respective weight ratios of 45:45:10.

42. The result of infrared spectroscopy showed that almost all absorption bands as well as the absorption band at 939 and 1638 cm' by a double bond are coincident with the absorption band of Bis-GMA, whereas the absorption band (3400 cm$^{-1}$) caused by the hydroxyl group was greatly decreased.

Example 2

Preparation of sealant composition based on 50:50 wt % prepolymer mixture of Bis-GMA and Tri-GMA 43. Multifunctional prepolymer prepared in Example 1 was separated into Bis-GMA, Tri-GMA, and Tetra-GMA, respectively, through the use of a column. The separated Tri-GMA and the existing Bis-GMA were mixed at 50:50 wt %. Bis-GMA (21 wt %) and 21 wt % of Tri-GMA were used as a prepolymer, and 45 wt % of TEGDMA, 9 wt % of silica, 0.9 wt % of CQ, 0.9 wt % of EDMAB, 1.7 wt % of HQ, 0.4 wt % of Tinuvin, 0.1 wt % of Irganox, and a small amount of inorganic pigment based on the total weight of the composition were added thereto.

44. With respect to this procedure, the diluent, the inorganic filler, and the polymerization inhibitor were first added to the prepolymer mixture and mixed to uniformly disperse a large quantity of the inorganic filler and, subsequently, the photoinitiator, the reductant, and other additives were added and uniformly dispersed to prepare a photo-cured dental pit and fissure sealant composition for caries prevention.

Example 3

Preparation of sealant composition based on 45:45:10 wt % prepolymer mixture of Bis-GMA. Tri-GMA and Tetra-GMA 45. The prepolymer mixture (38 wt %), 48 wt % of EGDMA, 9 wt % of silica, 0.9 wt % of CQ, 1.8 wt % of DMAEMA, 1.7 wt % of HQ, 0.4 wt % of Tinuvin 0.1 wt % of Irganox, and a small amount of inorganic pigment based on the total weight of the composition were added in the procedure described in example 2 to prepare a photo-cured dental pit and fissure sealant composition for caries prevention.

Example 4

Preparation of sealant composition based on 75:25 wt % prepolymer mixture of Bis-GMA and Tri-GMA 46. Bis-GMA (27 wt %), 9 wt % of Tri-GMA, 50 wt % of DEGDMA, 0.9 wt % of CQ, 1.8 wt % of EDMAB, 2.8 wt % of HQ monomethyl ether, 9 wt % of barium glass/silica, 0.4 wt % of Tinuvin, 0.1 wt % of BHT, and a small amount of inorganic pigment based on the total weight of the composition were added in the procedure described in example 2 to prepare a photo-cured dental pit and fissure sealant composition for caries prevention.

Example 5

Preparation of sealant composition based on 25:75 wt % prepolymer mixture of Bis-GMA and Tri-GMA 47. Bis-GMA (10 wt %), 30 wt % of Tri-GMA, 40 wt % of TEGDMA, 0.9 wt % of CQ, 1.8 wt % of DMAEMA, 1.8 wt % of HQ monoethyl ether, 9 wt % of barium glass, 0.4 wt % of Tinuvin, 0.1 wt % of Irganox, and a small amount of inorganic pigment based on the total weight of the composition were added in the procedure described in example 2 to prepare a photo-cured dental pit and fissure sealant composition for caries prevention.

Comparative Example 1

Preparation of sealant composition based on only Bis-GMA prepolymer itself

48. Bis-GMA (45 wt %), 42 wt % of TEGDMA, 9 wt % of silica, 0.9 wt % of CQ, 0.9 wt % of EDMAB, 1.7 wt % of HQ, 0.4 wt % of Tinuvin, 0.1 wt % of Irganox, and a small amount of inorganic pigment based on the total weight of the composition were added in the procedure described in example 2 to prepare a photo-cured dental pit and fissure sealant composition for caries prevention.

Comparative Example 2

Preparation of sealant composition based on only Tri-GMA prepolymer itself

49. Tri-GMA (50 wt %), 36 wt % of EGDMA, 9 wt % of silica, 0.9 wt % of CQ, 1.8% of DMAEMA, 1.8% of HQ, 0.4 wt % of Tinuvin, 0.1% of Irganox, and a small amount of inorganic pigment based on the total weight of the composition were added in the procedure described in example 2 to prepare a photo-cured dental pit and fissure sealant composition for caries prevention.

50. Table 3 shows the estimated results of the physical properties of the composition prepared in the examples and comparative examples.

TABLE 3

Physical property estimated result

| | Example | | | | Comparative example | |
|---|---|---|---|---|---|---|
| Physical property factor | 2 | 3 | 4 | 5 | 1 | 2 |
| Photoconversion (%) | 50 | 50 | 48 | 47 | 45 | 40 |
| Flexural strength (MPa) | 52 | 52 | 48 | 49 | 47 | 48 |
| Water absorption ($\mu$g/mm$^3$) | 2.3 | 2.1 | 4.6 | 3.3 | 5.5 | 1.2 |
| Solubility ($\mu$g/mm$^3$) | 0.6 | 0.5 | 1.1 | 0.6 | 1.3 | 0.4 |
| Two-body abrasion ($\mu$m) | 181.3 | 181.3 | 186.7 | 188.9 | 186.5 | 187.3 |
| Surface hardness ([HV 0.1/10]) | 16.2 | 16.2 | 15.7 | 14.9 | 13 | 14 |
| Diametral tensile strength (MPa) | 28.0 | 28.2 | 26.7 | 25.3 | 26.2 | 25.1 |
| Cytotoxicity (RI) | 0/1 | 0/1 | 1/1 | 1/1 | 1/1 | 1/1 |

51. As mentioned above, the photo-cured dental pit and fissure sealant composition for caries prevention in accordance with the present invention has better physical and mechanical properties, such as photoconversion, flexural strength, water absorption and solubility, two-body abrasion, surface hardness, and diametral tensile strength, and a level of cytotoxicity that is greater than that which is found in a Bis-GMA- or Tri-GMA based dental pit and fissure sealant composition. Particularly, the dental pit and fissure sealant composition based on the 50:50 wt % mixture of Bis-GMA and Tri-GMA shows the best results. Accordingly, the dental pit and fissure sealant composition based on the 50:50 wt % mixture of Bis-GMA and Tri-GMA has improved biocompatibility as well as physical and mechanical properties to provide a photo-cured dental pit and fissure sealant composition effective for caries prevention.

What is claimed is:

1. A photo-cured dental pit and fissure sealant composition for caries prevention comprising the components:

(A) 15 to 80 wt % of a prepolymer mixture comprising:
(i) 2,2-bis-(4-(2-hydroxy-3-methacryloyloxypropoxy)phenyl)propane ("Bis-GMA") of formula 1:

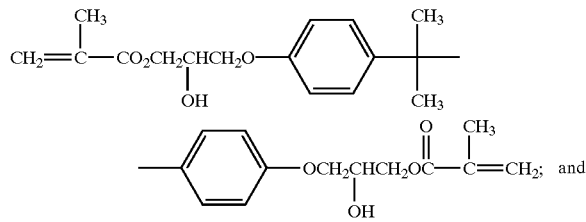

(ii) Tri-GMA of formula 2:

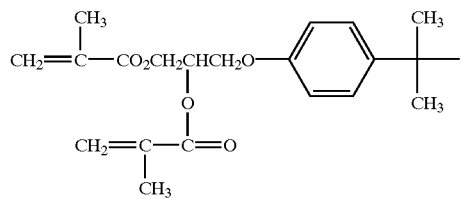

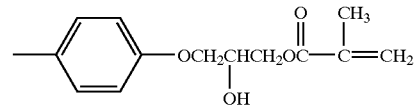

in the weight ratio of 95:5 to 5:95;

(B) 5 to 50 wt % of a diluent;
(C) 1 to 40 wt % of an inorganic filler;
(D) a photoinitiation system; and
(E) other additives, wherein the wt % of all the components are based on the total weight of the composition.

2. A photo-cured dental pit and fissure sealant composition for caries prevention comprising the components:

(A) 15 to 80 wt % of a prepolymer mixture comprising:
(i) 90 to 5 wt % of 2,2-bis-(4-(2-hydroxy-3-methacryloyloxypropoxy)phenyl)propane ("Bis-GMA") of formula 1:

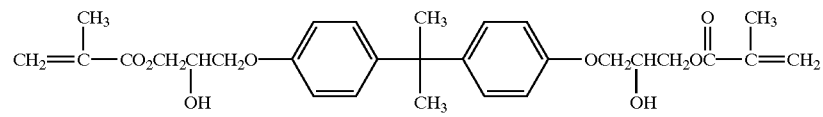

(ii) 90 to 5 wt % of Tri-GMA of formula 2:

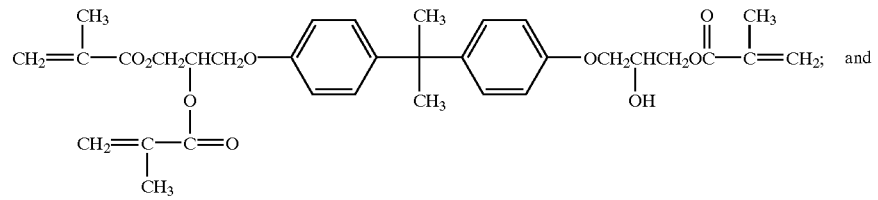

(iii) 90 to 5 wt % of Tetra-GMA of formula 3:

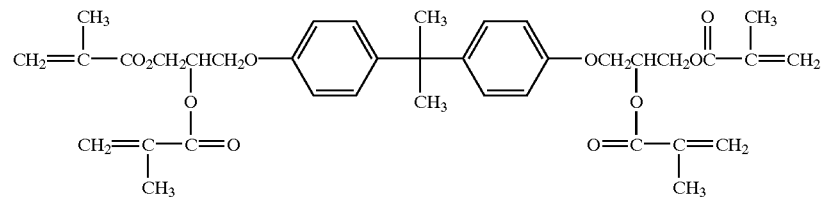

on the basis of the total weight of the prepolymer mixture (B) 5 to 50 wt % of a diluent;

(C) 1 to 40 wt % of an inorganic filler;

(D) a photoinitiation system; and (E) other additives, wherein the wt % of all the components are based on the total weight of the composition.

3. The photo-cured dental pit and fissure sealant composition for caries prevention according to claim 1 wherein the diluent is selected from the group consisting of: methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexane diol dimethacrylate, 1-methyl-1,3-propanediol dimethacrylate, and 1,6-bis(methacryloyloxy-2-ethoxycarbonylamino)-2,2,4-trimethylhexane.

4. The photo-cured dental pit and fissure sealant composition for caries prevention according to claim 2 wherein the diluent is selected from the group consisting of: methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexane diol dimethacrylate, 1-methyl-1,3-propanediol dimethacrylate, and 1,6-bis(methacryloyloxy-2-ethoxycarbonylamino)-2,2,4-trimethylhexane.

5. The photo-cured dental pit and fissure sealant composition for caries prevention according to claim 1 wherein the inorganic filler is selected from the group consisting of: silica, quartz, barium glass, barium glass/silica, barium glass mixture, quartz/barium glass, zirconia/silica, silica mixture, alumino silicate, lithium alumino silicate and barium aluminosilcate of particle size of 0.1 nm to 50 $\mu$m surface-treated with silane.

6. (New) The photo-cured dental pit and fissure sealant composition for caries prevention according to claim 2 wherein the inorganic filler is selected from the group consisting of: silica, quartz, barium glass, barium glass/silica, barium glass mixture, quartz/barium glass, zirconia/silica, silica mixture, alumino silicate, lithium alumino silicate and barium aluminosilcate of particle size of 0.1 nm to 50 $\mu$m surface-treated with silane.

7. The photo-cured dental pit and fissure sealant composition for caries prevention according to claim 5 wherein the silane for surface treatment of inorganic filler is selected from the group consisting of: trimethoxysilylpropylmethacrylate ($\gamma$-MPS), dimethyl dichloro silane, hexamethylene disilazane, and dimethyl polysiloxane.

8. The photo-cured dental pit and fissure sealant composition for caries prevention according to claim 6 wherein the silane for surface treatment of inorganic filler is selected from the group consisting of trimethoxysilylpropylmethacrylate ($\gamma$-MPS), dimethyl dichloro silane, hexamethylene disilazane, and dimethyl polysiloxane.

9. The photo-cured dental pit and fissure sealant composition for caries prevention according to claim 1, wherein the photoinitiation system comprises 0.1 to 10 wt % of a photoinitiator and 0.1 to 10 wt % of a reductant on the basis of the total weight of the composition.

10. The photo-cured dental pit and fissure sealant composition for caries prevention according to claim 2 wherein the photoinitiation system comprises 0.1 to 10 wt % of a photoinitiator and 0.1 to 10 wt % of a reductant on the basis of the total weight of the composition.

11. The photo-cured dental pit and fissure sealant composition for caries prevention according to claim 9 wherein the photoinitiatior is camphoquinone, and the reductant is N,N-dimethylaminoethyl methacrylate or ethyl p-dimethyl aminobenzoate.

12. The photo-cured dental pit and fissure sealant composition for caries prevention according to claim 7 wherein the photoinitiatior is camphoquinone, and the reductant is N,N-dimethylaminoethyl methacrylate or ethyl p-dimethyl aminobenzoate.

13. The photo-cured dental pit and fissure sealant composition for caries on according claim 1 wherein the other additives comprise 0.1 to 10 wt % of a polymerization inhibitor, 0.01 to 5 wt % of a lightstabilizer, 0.01 to 5 wt % of an antioxidant and 0.001 to 0.5 wt % of a pigment on the basis of the total weight of the composition.

14. The photo-cured dental pit and fissure sealant composition for caries prevention according claim 2 wherein the other additives comprise 0.1 to 10 wt % of a polymerization inhibitor, 0.01 to 5 wt % of a lightstabilizer, 0.01 to 5 wt % of an antioxidant and 0.001 to 0.5 wt % of a pigment on the basis of the total weight of the composition.

15. The photo-cured dental pit and fissure sealant composition for caries prevention according to claim 12 wherein the polymerization inhibitor is selected from the group consisting of hydroquinone, hydroquinone monomethyl ether and hydroquinone monoethyl ether; the lightstabilizer is 2-(2H-benzotriazol-2-yl)p-cresol; the antioxidant is (ethylenebis(oxyethylene)bis-(3-(5-tert-butyl-4-hydroxy-m-tolyl)-propionate or 2,6-di-tert-butyl-4-methylphenol; and the pigment is iron oxides or titanium dioxide inorganic pigment.

16. The photo-cured dental pit and fissure sealant composition for caries prevention according to claim 14 wherein the polymerization inhibitor is selected from the group consisting of hydroquinone, hydroquinone monomethyl ether and hydroquinone monoethyl ether; the lightstabilizer is 2-(2H-benzotriazol-2-yl)p-cresol; the antioxidant is (ethylenebis(oxyethylene)bis-(3-(5-tert-butyl-4-hydroxy-m-tolyl)-propionate or 2,6-di-tert-butyl-4-methylphenol; and the pigment is iron oxides or titanium dioxide inorganic pigment.

* * * * *

UNITED STATES PATENT AND TRADEMARK OFFICE
CERTIFICATE OF CORRECTION

PATENT NO.     : 6,573,312 B2
DATED          : June 3, 2003
INVENTOR(S)    : Han et al.

It is certified that error appears in the above-identified patent and that said Letters Patent is hereby corrected as shown below:

<u>Title page,</u>
Item [73], Assignee, Item [73] should read:

-- [73] Assignees:     Korea Institute of Science and Technology, Seoul (KR);
Dentkist Co., Ltd., Seoul (KR) --

Signed and Sealed this

Ninth Day of September, 2003

JAMES E. ROGAN
*Director of the United States Patent and Trademark Office*